US006265716B1

(12) United States Patent
Hunter et al.

(10) Patent No.: US 6,265,716 B1
(45) Date of Patent: Jul. 24, 2001

(54) VOLATILE MATRICES FOR MATRIX-ASSISTED LASER DESORPTION/IONIZATION MASS SPECTROMETRY

(75) Inventors: Joanna M. Hunter, Castro Valley; Hua Lin, Fremont; Christopher H. Becker, Palo Alto, all of CA (US)

(73) Assignee: GeneTrace Systems, Inc., Alameda, CA (US)

( * ) Notice: Subject to any disclaimer, the term of this patent is extended or adjusted under 35 U.S.C. 154(b) by 0 days.

(21) Appl. No.: 09/515,357

(22) Filed: Feb. 29, 2000

Related U.S. Application Data

(63) Continuation of application No. 09/086,993, filed on May 29, 1998, now Pat. No. 6,104,028.

(51) Int. Cl.$^7$ .................................................. H01J 44/04
(52) U.S. Cl. ............................................................ 250/288
(58) Field of Search .................................. 250/288, 281, 250/282; 436/173

(56) References Cited

U.S. PATENT DOCUMENTS

| | | |
|---|---|---|
| 4,775,619 | 10/1988 | Urdea . |
| 4,920,264 | 4/1990 | Becker . |

(List continued on next page.)

FOREIGN PATENT DOCUMENTS

| | | |
|---|---|---|
| WO 91/11533 | 8/1991 | (WO) . |
| WO 91/15600 | 10/1991 | (WO) . |
| WO 93/08305 | 10/1992 | (WO) . |
| WO 94/16090 | 1/1994 | (WO) . |
| WO 94/11530 | 5/1994 | (WO) . |
| WO 94/16101 | 7/1994 | (WO) . |
| WO 95/07361 | 3/1995 | (WO) . |
| WO 95/04160 | 9/1995 | (WO) . |
| WO 96/29431 | 9/1996 | (WO) . |
| WO 96/32504 | 10/1996 | (WO) . |
| WO 96/37630 | 11/1996 | (WO) . |
| WO 97/33000 | 3/1997 | (WO) . |
| WO 97/27327 | 7/1997 | (WO) . |

OTHER PUBLICATIONS

Abrams, et al,. "Comprehensive Detection of Single Base Changes in Human Genomic DNA Using Denaturing Gradient Gel Electrophoresis and a GC Clamp," *Genomics*, 7:463–475, 1990.

Arnott et al., "Construction and performance of a laser desorption/ionization TOF mass spectrometer system: applications to problems in peptide, protein, and DNA structural analysis," The 40th ASMS Conference on Mass Spectrometry and Allied Topics, May 31–Jun. 5, Washington, D.C., pp. 328–329, 1992.

Bai, Jian, et al., "Matrix–Assisted Laser Desorption/Ionization Mass Spectrometry of Restriction Enzyme–Digested Plasmid DNA Using an Active Nafion Substrate," *Rapid Commun. in Mass Spectrometry* 8:687–691, 1994.

(List continued on next page.)

*Primary Examiner*—Kiet T. Nguyen
(74) *Attorney, Agent, or Firm*—Angela P. Horne; Jonathan Alan Quine; Law Offices of Jonathan Alan Quine

(57) ABSTRACT

A sample preparation method is disclosed for volatilization and mass spectrometric analysis of nonvolatile high molecular weight molecules. Photoabsorbing molecules having significant sublimation rates at room temperature under vacuum, and preferably containing hydroxy functionalities, are disclosed for use as matrices in matrix-assisted laser desorption/ionization mass spectrometry. The samples are typically cooled in the mass spectrometer to temperatures significantly below room temperature.

23 Claims, 2 Drawing Sheets

U.S. PATENT DOCUMENTS

| | | |
|---|---|---|
| 4,935,357 | 6/1990 | Szybalski . |
| 5,003,059 | 3/1991 | Brennan . |
| 5,064,754 | 11/1991 | Mills . |
| 5,075,217 | 12/1991 | Weber . |
| 5,118,937 | 6/1992 | Hillenkamp et al. . |
| 5,135,870 | 8/1992 | Williams et al. . |
| 5,288,644 | 2/1994 | Beavis et al. . |
| 5,364,759 | 11/1994 | Caskey et al. . |
| 5,369,004 | 11/1994 | Polymeropoulos et al. . |
| 5,378,602 | 1/1995 | Polymeropoulos et al. . |
| 5,464,985 | 11/1995 | Cornish et al. . |
| 5,468,610 | 11/1995 | Polymeropoulos et al. . |
| 5,503,980 | 4/1996 | Cantor . |
| 5,508,169 | 4/1996 | Deugau et al. . |
| 5,547,835 | 8/1996 | Koster . |
| 5,580,773 | 12/1996 | Levis et al. . |
| 5,582,979 | 12/1996 | Weber . |
| 5,599,666 | 2/1997 | Schumm et al. . |
| 5,605,798 | 2/1997 | Köster . |
| 5,622,824 | 4/1997 | Köster . |
| 5,625,184 | 4/1997 | Vestal et al. . |
| 5,627,369 | 5/1997 | Vestal et al. . |
| 5,691,141 | 11/1997 | Köster . |
| 5,700,642 | 12/1997 | Monforte et al. . |
| 5,854,486 * | 12/1998 | Dreyfus ................................. 250/285 |
| 6,104,028 * | 8/2000 | Hunter et al. ........................ 250/288 |

OTHER PUBLICATIONS

Bai, Jian, et al., "Procedures for Detection of DNA by Matrix–Assisted Laser Desorption/Ionization Mass Spectrometry Using a Modified Nafion Film Substrate," *Rapid Commun. in Mass Spectrometry*, 9:1172–1176, 1995.

Benner and Jaklevic, "DNA Base–Pair Substitutions Detected in Double–Stranded DNA With Matrix–Assisted Laser Desorption/Ionization Time–of–Flight Mass Spectrometry," *Eur. Mass Spectrum.*, 479–485, 1995.

Benner, Horn, Katz, Jaklevic, "Identification of Denatured Double–stranded DNA by Matrix–Assisted Laser Desorption/Ionization Time–of–Flight Mass Spectrometry," *Rapid Commun. in Mass Spectrom.*, 9:537–540, 1995.

Bergh, et al., "Complete Sequencing of the p53 Gene Provides Prognostic Information in Breast Cancer Patients, Particularly in Relation to Adjuvant Systemic Therapy and Radiotherapy," *Nature Medicine*, 1:1029–1034, 1995.

Bevan et al., "The analysis of oligonucleotides and their phosphoramidate analogues by LSIMS mass spectrometry," The 39th ASMS Conference on Mass Spectrometry and Allied Topics, pp. 983–984, 1989.

Chang, et al., "Detection of ΔF508 Mutation of the Cystic Fibrosis Gene by Matrix–Assisted Laser Desorption/Ionization Mass Spectrometry," *Rapid Commun. in Mass Spectometry*, 9:772–774, 1995.

Edmonds et al., "Electrospray ionization mass spectrometry and tandem mass spectrometry of small oligonucleotides," 37th ASMS Conference on Mass Spectrometry and Allied Topics, May 21–26, Miami Beach, FL, pp. 844–845, 1989.

Fang, et al., "Simultaneous Analysis of Mutant and Normal Alleles for Multiple Cystic Fibrosis Mutations by the Ligase Chain Reaction," *Human Mutation*, 6:144–151, 1995.

Fenn, et al., "Electrospray Ionization for Mass Spectrometry Large Biomolecules," *Science*, 246:64–71, 1989.

Gimon et al., "Are Proton Transfer Reactions of Excited States Involved in UV Laser Desorption Ionization?," *Organic Mass Spectrometry*, 27:827–830, 1992.

Hegner, Wagner, Semenza, "Ultralarge Atomically Flat Template–Stripped Au Surfaces for Scanning Probe Microscopy," *Surface Science*, 291:39–46, 1993.

Hunter et al., "Cryogenic Frozen Solution Matrices for Analysis of DNA by Time–of–Flight Mass Spectrometry," *Analytical Chemistry*, 69:3608–12, 1997.

Huppert et al., "Laser Studies of Proton Transfer," *Advances in Chemical Physics*, 47:643–679, 1981.

Jacobson et al., "Applications of mass spectrometry to DNA sequencing,", *GATA*, 8(8):223–229, 1991.

Jurinke, Christian, et al., "Analysis of Ligase Chain Reaction Products Via Matrix–Assisted Laser Desorption/Ionization Time–of–Flight–Mass Spectrometry," *Analytical Biochemistry*, 237:174–181, 1996.

Karas and Bahr, "Matrix–assisted laser desorption ionization mass spectrometry," *Mass Spectrometry Reviews*, 10:335–357, 1991.

Kirpekar, Nordhoff, Kristiansen, Roepstorff, Lezius, Hahner, Karas, Hillenkamp, "Matrix Assisted Laser Desorption/Ionization Mass Spectrometry of Enzymatically Synthesized RNA Up to 150 kDa," *Nucleic Acis Research*, 22(19):3866–3870, 1994.

Kuimelis and McLaughlin, "Cleavage Properties of an Oligonucleotide Containing a Bridged Internucleotide 5'–phosphorothioate RNA Linkage," *Nucleic Acids Research*, 23:4753–4760, 1995.

Lee, et al., Comparison on Short Tandem Repeat (STR) Detection Using Silver, Fluorescence and Matrix Assisted Laser Desorption Ionization Time–of–Flight Mass Spectrophotometry (MALDITOF–MS), Proceedings of the Sixth International Symposium on Human Identification, published by Promega Corp., 1995.

Lee, et al., "DNA Sequencing with Dye–Labeled Terminators and T7 DNA Polymerase: Effect of Dyes and dNTPs on Incorporation of Dye–Terminators and Probability Analysis of Termination Fragments," *Nucleic Acids Research*, 20(10):2471–2483, 1992.

Liang, Gangning, et al., "The Use of 2–Hydroperoxytetrahydrofuran as a Reagent to Sequence Cytosine and to Probe Non–Watson–Crick DNA Structures," *Nucleic Acids Research*, 23(4):713–719, 1995.

Limbach et al., "Characterization of oligonucleotides and nucleic acids by mass spectrometry," *Current Opinion Biotechnology*, 6:96–102, 1995.

Liu, Yan–Hui, et al., "Rapid Screening of Genetic Polymorphisms Using Buccal Cell DNA with Detection by Matrix––Assisted Laser Desorption/Ionization Mass Spectrometry," *Rapid Commun. in Mass Spectrometry*, 9:735–743, 1995.

Liu, Yan–Hui, et al., "Use of a Nitrocellulose Film Substrate in Matrix–Assisted Laser Desorption/Ionization Mass Spectrometry for DNA Mapping and Screening," *Anal. Chem.*, 67:3482–3490, 1995.

Mag, et al., "Synthesis and Selective Cleavage of an Oligodeoxynucleotide Containing a Bridged Internucleotide 5'–Phosphorothioate Linkage," *Nucleic Acids Research*, 19(7):1437–1441, 1991.

McNeal et al., "A new method for the analysis of fully protected oligonucleotides by $^{252}$Cf–plasma desorption mass spectrometry. 3. Positive ions," *J. Am. Chem. Soc.*, 104:981–984, 1982.

Mizusawa et al., "Improvement of the dideoxy chain termination method of DNA sequencing by use of deoxy–7–deazaguanosine triphosphate in place of dGTP," *Nucl. Acids Res.*, 14(3):1319–1325, 1986.

Mock et al., "Sample immobilization protocols for matrix assisted laser desorption mass spectrometry," The 40th ASMS Conference on Mass Spectrometry and Allied Topics, pp. 1921–1922, 1992.

Musser and Kelley, "Sensitivity enhancement for static and continuous flow FAB/MS analysis of nucleotides by quaternary amine surfactants," The 39th ASMS Conference on Mass Spetrometry and Allied Topics, pp. 374–375, 1989.

Nelson, Dogruel, Williams, "Detection of Human IgM at m/z~1 Mda," Rapid Commun. in Mass Spectrom., 9:7, 1995.

Newman, Nwosu, Williams, Cosstick, Seela, Connolly, "Incorporation of a Complete Set of Deoxyadenosine and Thymidine Analogues Suitable for the Study of Protein Nucleic Acid Interactions into Oligodeoxynucleotides," Biochemistry, 29:9891–9901, 1990.

Nordhoff et al., "Matrix–assisted laser desorption/ionization mass spectrometry of nucleic acids with wavelengths in the ultraviolet and infrared," Rapid Comm. Mass Spectrometry, 6:771–776, 1992.

Orita, et al., "Detection of Polymorphisms of Human DNA by Gel Electrophoresis as Single–Strand Conformation Polymorphisms," Proc. Natl. Acad. Sci. USA, 86:2766–2770, 1989.

Overberg et al., "Laser desorption mass spectrometry, Part II performance and applications of mastrix–assisted laser desorption/ionization of large biomolecules," Anal. Chem., 181–197, 1992.

Parr et al., "Matrix–assisted laser desorption/ionization mass spectrometry of synthetic oligodeoxyribonucleotides," Rapid Comm. Mass Spectrometry, 6:369–372, 1992.

Pease, et al., "Light–Generated Oligonucleotide Arrays for Rapid DNA Sequence Analysis," Proc. Natl. Acad. Sci. USA, 91:5022–5026, 1994.

Richterich, et al., "Cytosine Specific DNA Sequencing with Hydrogen Peroxide," Nucleic Acids Research, 23(23):4922–4923, 1995.

Saleeba, et al., "Chemical Cleavage of Mismatch to Detect Mutations," Methods Enzymology, 217:286–295, 1993.

Sandaltzopoulus and Becker "Solid–Phase DNase I Footprinting," Biochemica, 4:25–27, 1995.

Sedlak, "GeneTrace Systems Bets its Future in Genomics on TOF Mass Spectroscopy," Genetic Engineering News, 16(21):, 1996. (website: http://www.genetrace.com).

Shaler, et al., "Effect of Impurities on the Matrix–Assisted Laser Desorption Mass Spectra of Single–Stranded Oligodeoxynucleotides," Anal. Chem., 68(3):576–579, 1996.

Shaw, Madison, Sood, Spielvogel, "Oligonucleoside Boranophosphate (Borane Phosphonate)," In: Methods in Molecular Biology, vol. 20: Protocols for Oligonucleotides and Analogs, S. Agrawal (Ed.), Humana Press Inc., Totowa, NJ, Chapter 11, 224–243, 1993.

Soukup, Cerny, Maher III, "Preparation of Oligonucleotide—Biotin Conjugates with Cleavable Linkers," Bioconjugate Chem., 6:135–138, 1995.

Spengler et al., "Molecular weight determination of underivatized oligodeoxyribonucleotides by positive–ion matrix–assisted ultraviolet laser–desorption mass spectrometry," Rapid Comm. Mass Spectrometry, 4(4):99–102, 1990.

Spengler, et al., "Laser Mass Analysis in Biology," Ber.Bunsenqes Phys. Chem., 93(3):396–402, 1989.

Stahl et al., "Solid phase DNA sequencing using the biotin–avidin system," Nucl. Acids Res., 16(7):3025–3039, 1988.

Stults and Marsters, "Characterization of oligodeoxynucleotide conjugates by electrospray ionization mass spectrometry," Proceedings of the 39th ASMS Conference on Mass Spectrometry and Allied Topics, May 19–24, Nashville, TN, pp. 1161–1162, 1991.

Stults and Marsters, "Improved electrospray ionization of synthetic oligodeoxynucleotides," Rapid Comm. Mass Spectrometry, 5:359–363, 1991.

Szybalski, "Universal Restriction Endonucleases: Designing Novel Cleavage Specificities by Combining Adapter Oligodeoxynucleotide and Enzyme Moieties," Gene, 40:169–173, 1985.

Tanaka, et al., "Protein and Polymer Analyses up to m/z 100 000 by Laser Ionization Time–of–flight Mass Spectrometry," Rapid Commun. in Mass Spectrometry, 2:151–153, 1988.

Tang et al., "Detection of 500–Nucleotide DNA by Laser Desorption Mass Spectrometry," Rapid Commun. in Mass Spectrometry, 8(9):727–730, 1994.

Tang, et al., "Laser Mass Spectrometry of Polydeoxyribothymidylic Acid Mixtures," Rapid Commun. Mass Spectrom, 7:63–66, 1993.

Tang, et al., "Matrix–Assisted Laser Desorption/Ionization of Restriction Enzyme–Digested DNA," Rapid Commun. in Mass Spectrometry, 8:183–186, 1994.

Tong and Smith, "Solid–phase method for the purification of DNA sequencing reactions," Anal. Chem., 64:2672–2677, 1992.

Trainor, "DNA sequencing, automation, and the human genome," Anal. Chem., 62:418–426, 1990.

Uhlmann and Peyman "Antisense Oligonucleotides: A New Therapeutic Principle," Chemical Reviews, 90(4):543–584, 1990.

Wang, et al., "DNA Sequencing from Single Phage Plaques Using Solid–Phase Magnetic Capture," BioTechniques, 18(1):130–135, 1995.

Wu, et al., "Matrix–Assisted Laser Desorption Time–of–Flight Mass Spectrometry of Oligonucleotides Using 3–Hydroxypicolinic Acid as an Ultraviolet–sensitive Matrix," Rapid Commun. in Mass Spectrometry, 7:142–146, 1993.

Wu, Shaler, Becker, "Time–of–Flight Mass Spectrometry of Underivatized Single–Stranded DNA Oligomers by Matrix–Assisted Laser Desorption," Anal. Chem., 66:1637–1645, 1994.

Youil, et al., "Screening for Mutations by Enzyme Mismatch Cleavage with T4 Endonuclease VII," Proc. Natl. Acad. Sci. USA, 92:87–91, 1995.

* cited by examiner

VOLATILE MATRICES FOR MATRIX-ASSISTED LASER DESORPTION/IONIZATION MASS SPECTROMETRY

This application is a continuation of and claims the benefit of U.S. application Ser. No. 09/086,993 filed May 29, 1998, now U.S. Pat. No. 6,104,028.

The government may own rights in the present invention pursuant to Grant No. R01 HG-00174 from the National Institutes of Health.

BACKGROUND OF THE INVENTION

1. Field of the Invention

This invention relates to volatile photoabsorbing matrices having a low sublimation temperature for use in the mass spectrometric analysis of large, nonvolatile molecules. This invention also relates to methods for preparing samples containing large, nonvolatile analyte molecules for laser desorption mass spectrometry employing such matrices.

2. Description of Related Art

Approximately 4,000 human disorders are attributed to genetic causes. Hundreds of genes responsible for various disorders have been mapped, and sequence information is being accumulated rapidly. A principal goal of the Human Genome Project is to find all genes associated with each disorder. The definitive diagnostic test for any specific genetic disease (or predisposition to disease) will be the identification of polymorphic variations in the DNA sequence of affected cells that result in alterations of gene function. Furthermore, response to specific medications may depend on the presence of polymorphisms. Developing DNA (or RNA) screening as a practical tool for medical diagnostics requires a method that is inexpensive, accurate, expeditious, and robust.

Genetic polymorphisms and mutations can manifest themselves in several forms, such as point polymorphisms or point mutations where a single base is changed to one of the three other bases; deletions where one or more bases are removed from a nucleic acid sequence and the bases flanking the deleted sequence are directly linked to each other; insertions where new bases are inserted at a particular point in a nucleic acid sequence adding additional length to the overall sequence; and expansions and reductions of repeating sequence motifs. Large insertions and deletions, often the result of chromosomal recombination and rearrangement events, can lead to partial or complete loss of the activity of a gene. Of these forms of polymorphism, in general the most difficult type of change to screen for and detect is the point polymorphism because it represents the smallest degree of molecular change.

Although a number of genetic defects can be linked to a specific single point mutation within a gene, e.g. sickle cell anemia, many are caused by a wide spectrum of different mutations throughout the gene. A typical gene that might be screened could be anywhere from 1,000 to 100,000 bases in length, though smaller and larger genes do exist. Of that amount of DNA, only a fraction of the base pairs actually encode the protein. These discontinuous protein coding regions are called exons and the remainder of the gene is referred to as introns. Of these two types of regions, exons often contain the most important sequences to be screened. Several complex procedures have been developed for scanning genes in order to detect polymorphisms. These procedures are applicable to both exons and introns.

In terms of current use, most of the methods to scan or screen genes employ slab or capillary gel electrophoresis for the separation and detection step in the assays. Gel electrophoresis of nucleic acids primarily provides relative size information based on mobility through the gel matrix. If calibration standards are employed, gel electrophoresis can be used to measure absolute and relative molecular weights of large biomolecules with some moderate degree of accuracy; even then, the accuracy is typically only 5% to 10%. Also the molecular weight resolution is limited. In cases where two DNA fragments with the identical number of base pairs can be separated, for example, by using high concentration polyacrylamide gels, it is still not possible to identify which band on a gel corresponds to which DNA fragment without performing secondary labeling experiments. Thus, gel electrophoresis techniques can only determine size and cannot provide any information about changes in base composition or sequence without performing more complex sequencing reactions. Gel-based techniques, for the most part, are dependent on labeling or staining methods to visualize and discriminate between different nucleic acid fragments.

Many methods in use today capable of screening broadly for genetic polymorphisms suffer from technical complication and are labor and time intensive. Single strand conformational polymorphism (SSCP) (Orita et al., 1989), denaturing gradient gel electrophoresis (DGGE) (Abrams et al., 1990), chemical cleavage at mismatch (CCM) (Saleeba and Cotton, 1993), enzymatic mismatch cleavage (EMC) (Youil et al., 1995), and cleavage fragment length polymorphism (CFLP) procedures are currently gel-based, making them cumbersome to automate and perform efficiently. Thus, there is a need for new methods that can provide cost effective and expeditious means for screening genetic material in an effort to detect genetic mutations and diagnose related medical conditions simply, quickly, accurately, and inexpensively.

Another approach that is having some success is to employ mass spectrometry to screen for and detect genetic mutations as well as to sequence nucleic acids. In order to measure the mass of nonvolatile high molecular weight molecules, typically greater than 1000 Da, in a mass spectrometer, the analyte molecules must first be volatilized or converted into gas-phase ions. Although direct laser desorption of the neat analyte is one approach to volatilizing the molecule, the energy deposited into the analyte may induce fragmentation and lead to results that are ambiguous or difficult to analyze. The late 1980's saw the rise of two new mass spectrometric techniques which are potentially suitable for genetic screening tests by successfully measuring the masses of intact very large biomolecules, namely, matrix-assisted laser desorption/ionization (MALDI) time-of-flight mass spectrometry (TOF MS) (Tanaka et al., 1988; Spengler et al., 1989) and electrospray ionization (ES) combined with a variety of mass analyzers. The MALDI mass spectrometric technique can also be used with methods other than time-of-flight, for example, magnetic sector, Fourier-transform ion cyclotron resonance, quadrupole, and quadrupole trap.

MALDI-TOF MS involves laser pulses focused on a small sample plate on which analyte molecules (i.e. nucleic acids) are embedded in either a solid or liquid matrix which is typically a small, highly absorbing material, such as a small aromatic organic molecule. The volatilization of intact fragile molecules benefits from the use of matrix-assisted laser desorption ionization because the radiative energy from the laser pulse is coupled indirectly into the analyte through the matrix molecules. Typically, the analyte molecules are crystallized with a large molar excess of a photoabsorbing matrix (see U.S. Pat. Nos. 4,920,264 and 5,118,937, incorporated herein by reference). An advance in MALDI analysis of polynucleotides was the discovery of 3-hydroxypicolinic acid (3-HPA) as a suitable matrix for mixed-base oligonucleotides (Wu, et al., 1993).

The laser pulses transfer energy to the matrix causing a microscopic ablation and concomitant ionization of the analyte molecules, producing a gaseous plume of intact, charged nucleic acids in single-stranded form. It is thought that upon laser excitation the matrix molecules are rapidly heated and ejected into the gas phase, carrying analyte molecules into the expansion plume of molecules and ions. It is thought that gas-phase ion-molecule collisions subsequently ionize the neutral analyte molecules in the near-surface region, often via proton transfer. The matrix thus functions as both an energy- and charge-transfer species. If double-stranded nucleic acids are analyzed, the MALDI-TOF MS typically results in detection of mostly charged denatured single-stranded nucleic acids.

The ions generated by the laser pulses are accelerated to a fixed kinetic energy by a strong electric field and then passed through an electric field-free region in vacuum, traveling with a velocity corresponding to their respective mass-to-charge ratios (m/z). Thus, the smaller m/z ions will travel through the vacuum region faster than the larger m/z ions thereby causing a separation. At the end of the electric field-free region, the ions collide with a detector that generates a signal as each set of ions of a particular mass-to-charge ratio strikes the detector. Usually for a given assay, 10 to 100 mass spectra resulting from individual laser pulses are summed together to make a single composite mass spectrum with an improved signal-to-noise ratio.

The mass of an ion (such as a charged nucleic acid) is measured by using its velocity to determine the mass-to-charge ratio by time-of-flight analysis. In other words, the mass of the molecule directly correlates with the time it takes to travel from the sample plate to the detector. The entire process takes only microseconds. In an automated apparatus, tens to hundreds of samples can be analyzed per minute. In addition to speed, MALDI-TOF MS has one of the largest mass ranges for mass spectrometric devices. The current mass range for MALDI-TOF MS is from 1 to 1,000,000 Da (measured recently for a protein) (Nelson et al., 1995).

The performance of a mass spectrometer is measured by its sensitivity, mass resolution and mass accuracy. Sensitivity is measured by the amount of material needed; it is generally desirable and possible with mass spectrometry to work with sample amounts in the femtomole and low picomole range. Mass resolution, m/$\Delta$m, is the measure of an instrument's ability to produce separate signals from ions of similar mass. Mass resolution is defined as the mass, m, of an ion signal divided by the full width of the signal, $\Delta$m, usually measured between points of half-maximum intensity. Mass accuracy is the measure of error in designating a mass to an ion signal. The mass accuracy is defined as the ratio of the mass assignment error divided by the mass of the ion and can be represented as a percentage.

To be able to detect any point polymorphism directly by MALDI-TOF mass spectrometry, one would need to resolve and accurately measure the masses of nucleic acids in which a single base change has occurred (in comparison to the wild type nucleic acid). A single base change can be a mass difference of as little as 9 Da. This value represents the difference between the two bases with the closest mass values, A and T (A=2'-deoxyadenosine-5'-phosphate=313.19 Da; T=2'-deoxythymidine-5'-phosphate=304.20 Da; G=2'-deoxyguanosine-5'-phosphate=329.21 Da; and C=2'-deoxycytidine-5'-phosphate=289.19 Da). If during the mutation process, a single A changes to T or a single T to A, the mutant nucleic acid containing the base transversion will either decrease or increase by 9 Da in total mass as compared to the wild type nucleic acid. For mass spectrometry to directly detect these transversions, it must therefore be able to detect a minimum mass change, $\Delta$m, of approximately 9 Da.

For example, in order to fully resolve (which may not be necessary) a point-mutated (A to T or T to A) heterozygote 50-base single-stranded DNA fragment having a mass, m, of ~15,000 Da from its corresponding wild type nucleic acid, the required mass resolution is m/$\Delta$m=15,000/9≈1,700. However, the mass accuracy needs to be significantly better than 9 Da to increase quality assurance and to prevent ambiguities where the measured mass value is near the half-way point between the two theoretical masses. For an analyte of 15,000 Da, in practice the mass accuracy needs to be $\Delta$m~±3 Da=6 Da. In this case, the absolute mass accuracy required is (6/15,000)*100=0.04%. Often a distinguishing level of mass accuracy relative to another known peak in the spectrum is sufficient to resolve ambiguities. For example, if there is a known mass peak 1000 Da from the mass peak in question, the relative position of the unknown to the known peak may be known with greater accuracy than that provided by an absolute, previous calibration of the mass spectrometer.

In addition, the ability to separate DNA fragments (1) differing in only one base in length and (2) of reasonable length (e.g., of sizes corresponding to at least primer size, around 20 to 30 bases or so up to about 50 bases in length) is critical to achieving even rudimentary DNA sequencing by MALDI-MS. For laser desorption mass spectroscopy techniques to successfully analyze macromolecules requires that one stably laser-desorb molecules into a vapor phase, and separate and detect (and thereby determine the mass of) the volatilized molecules by mass spectroscopy. The ability to stably desorb the macromolecule depends on the availability of a suitable light absorbing matrix that will allow one to stably laser-desorb DNA molecules from a solid state to a gaseous state, and permit separation of DNA molecules having only a nucleotide or so difference in length. Putting that into perspective, the difference in mass between a polynucleotide having 30 versus 31 nucleotide represents about a 3% difference in mass (about 9610 v. 310, assuming an average m.w. of 310 for each nucleotide). If one applies this to a DNA molecule of 100 nucleotides in length, a modest sequence by DNA sequencing standards, the separation system must distinguish among DNA molecules differing by only 1% in mass.

Thus, there is a need for the development of MS techniques and related materials for practicing these techniques that have enhanced resolution, accuracy, and sensitivity. The ability to stably desorb the molecule from a solid matrix that absorbs light at the laser wavelength, without radiation damage and fragmentation of the sample is particularly important as fragmentation can lead to complex spectra and decreased resolution and sensitivity.

Although MALDI generates less energetic analyte ions than direct laser desorption, thus decreasing the thermal degradation of the analyte, the ions nevertheless contain significant internal energy, which may result in fragmentation. Among the few matrix molecules that have been found to desorb/ionize intact DNA, 3-HPA is currently the most widely used (Wu et al., 1993; Wu et al., 1994)). Using a matrix mixture of 3-HPA with picolinic acid, oligonucleotides have been detected that are greater than 500 bases (up to about 200 kDa) in length (Tang et al., 1994; Liu et al., 1995). However, as the length of the oligonucleotide increases, the mass resolution is degraded by widening kinetic energy spreads, prompt fragmentation, delayed fragmentation (metastable decay), and the formation of matrix adducts. Thus, there is a need to develop MS materials and methods that minimize fragmentation of the analyte ions during the MALDI process, extend the accessible mass range for mass spectrometric detection, and enhance the utility of the MS techniques.

SUMMARY OF THE INVENTION

It is therefore a goal of the present invention to provide compositions and methods relating to the preparation of samples containing nonvolatile analyte molecules for mass analysis using a photoabsorbing, low-sublimation temperature matrix. These matrix molecules provide a means for desorbing and ionizing nonvolatile, nonthermally-labile organic molecules such as biomolecules and synthetic polymers. Minimizing fragmentation of the parent analyte ion and/or reducing adduct formation leads to increased detection sensitivity and/or increased resolution and/or extension of the usable mass range.

The deleterious effects associated with widening kinetic energy spreads, fragmentation and the formation of matrix-analyte adducts are reduced by employing a matrix system, as disclosed herein, having lower intermolecular binding energies associated with increased volatility. Lower binding energies can reduce fragmentation by minimizing the internal energy of the desorbed analyte, and can reduce adduct formation by lowering the binding energy of the analyte with its surrounding molecules. The desorption of a volatile matrix at room temperature but cooled to maintain low vapor pressure in the mass spectrometer may also require less energy. Because a vacuum is required for the mass spectrometry, volatile, crystalline matrices which sublimate or evaporate readily at room temperature are typically cooled to reduce their vapor pressures to practical levels, which is below about $10^{-5}$ Torr in the desorption plume. This consequently means that the analyte internal energy may also be lower. It is therefore an advantage of the present invention to use liquids or low sublimation temperature solids as matrices because such systems generally enable lower desorption/ionization temperatures.

The present invention relates to a method for volatilization and mass spectrometric analysis of nonvolatile, or nonthermally labile, large organic molecules including biomolecules such as nucleic acids, for example, DNA and RNA; proteins and peptide nucleic acids (PNA); oligosaccharides, and other high molecular weight polymers.

The invention generally provides a method for determining the mass of a large organic molecule. The method typically includes contacting a large organic molecule, the mass of which one desires to determine, with a photoabsorbing, or light absorbing, low-sublimation temperature matrix to produce a matrix:molecule mixture. This contacting step may be carried out by dissolving the large organic molecule to be analyzed in a solution containing the matrix. The matrix:molecule mixture is then irradiated by a light source, such as a laser, to desorb, ionize, and produce an ionized large organic molecule. The ionized large organic molecule is then separated from other constituents, such as the matrix:molecule mixture or other matrix:molecule adducts, using mass spectrometry and the mass of the ionized large organic molecule determined. While any mass spectrometry is contemplated for use with the present invention, time-of-flight mass spectrometry is preferred.

The matrix:molecule mixture typically comprises a physical mixture of the matrix with the molecule to be analyzed. It may or may not contain adducts of the matrix with the molecule. Although if adducts are formed, they will typically be only weakly associated such that they may be readily dissociated upon irradiation, desorption, and ionization.

As used herein the term "a" encompasses embodiments wherein it refers to a single element as well as embodiments including one or more of such elements.

In performing the mass spectrometry, it is preferable to use a cooled sample stage. Generally, the sample stage is cooled to less than 273° K, typically to from about 150° K to 200° K or to about 180 K. While it is contemplated that the sample stage may be cooled by any suitable means, it may typically be cryogenically cooled by liquid nitrogen.

In creating the matrix:molecule mixture, for example, by dissolving the large organic molecule in a solution containing the matrix, one of skill in the art will understand that the solution containing the matrix may generally contain one or more solvents. Preferably the solvents will be water and/or organic solvents, such as ethanol, methanol, toluene, acetone, and acetonitrile. After the matrix:molecule mixture is formed, the solvents are substantially evaporated, typically to dryness. In preferred embodiments, the solvents are evaporated at room temperature. After evaporating the solvent, the resulting solid or crystalline molecule-matrix mixture is cooled to a vapor pressure between about $10^{-10}$ Torr and about $10^{-5}$ Torr.

The matrix for use in the present invention is generally a volatile, light-absorbing, hydroxy-bearing matrix. As used herein, volatile matrices are those that are volatile at room temperature at ambient or reduced pressures. In preferred aspects, the matrix may be a phenol, a hydroxyquinoline, or a hydroxynaphthalene. Where the matrix is a phenol, it will preferably be 4-nitrophenol. Where the matrix is a hydroxyquinoline, it will preferably be 8-hydroxyquinoline. It is also generally preferred that the matrix have a molecular weight of between about 90 Da and about 400 Da. Different classes of analyte molecules may also require different matrix systems. The matrix should typically not react or interact strongly with the analyte and the analyte should be soluble in the matrix crystals.

In particular embodiments the matrix has a high sublimation rate between the temperatures of 20° C. to 200° C. (or a low sublimation temperature). The low-sublimation temperature matrix may typically have a sublimation rate at room temperature of at least 0.1 $\mu$m·min$^{-1}$ at a pressure of about $10^{-5}$ Torr or less and preferably the sublimation rate at these conditions is from about 0.01 $\mu$m·min$^{-1}$ to about 0.1 mm·min$^{-1}$. Also provided are embodiments where the matrix is a crystalline solid.

As used herein the terms "photo absorbing" or "light absorbing" refer to the ability of the matrix to absorb the desorption light sufficiently strong to aid in the desorption and ionization of the large organic molecule. Typically the matrices will absorb light between the wavelengths of approximately 200 nm and approximately 20,000 nm although it will be understood that this absorption is not continuous. It is further preferred that the photoabsorbing matrix have an absorption coefficient greater than about 10 L·cm$^{-1}$·mol$^{-1}$, up to and including an absorption coefficient of $10^6$ L·cm$^{-1}$·mol$^{-1}$, at the wavelength of the desorbing and ionizing radiation. The method of the invention is useful for determining the mass of virtually any large organic molecule. For example, the mass of a polymer may be determined using the methods of the invention. In preferred aspects of the invention, the polymer to be analyzed will be a biopolymer, such as a nucleic acid, a polypeptide, a peptide nucleic acid (PNA), an oligosaccharide, or a mass-modified derivative thereof. Where the molecule to be analyzed is a nucleic acid, it will be understood that it may be, for example, a DNA or an RNA.

The analyte should typically be purified to minimize the presence of salt ions and other molecular contaminants. These impurities may reduce the intensity and quality of the mass spectrometric signal to a point where either (i) the signal is undetectable or unreliable, or (ii) the mass accuracy and/or resolution is below the value necessary for the particular application, such as to detect the type of polymorphism expected or sequence the analyte. A preferred method to purify the analyte is to immobilize it on a solid support and wash it remove impurities, such as sodium and potassium ions. The analyte may then be released from the solid support and contacted with the matrix.

The size of the analyte to be analyzed should also be within the range where there is sufficient mass resolution and accuracy. Mass accuracy and resolution significantly degrade as the mass of the analyte increases. Currently, the detection of single nucleotide polymorphisms (SNPs) above said mass value is difficult above a mass of approximately 30,000 Da for oligonucleotides (~100 bases) although this range may increase with further advances in MS-related technology. Third, because all molecules within a sample are visualized during mass spectrometric analysis (i.e. it is not possible to selectively label and visualize certain molecules and not others as one can with gel electrophoresis methods), samples may preferably be partitioned prior to analysis to remove unwanted products from the spectrum.

It is contemplated that the method of the invention will allow for the mass determination of any large organic molecule having a mass of greater than about 1,000 Da. More specifically, one may determine the mass of a molecule having a mass of greater than about 27,000 Da, greater than about 30,000 Da, greater than about 50,000 Da, greater than about 75,000 Da, greater than about 100,000 Da, greater than about 150,000 Da, greater than about 175,000 Da, greater than about 200,000 Da, greater than about 250,000 Da, or even greater than about 315,000 Da. The organic molecule will typically have a mass of less than 5,00,000 Da, 3,000,000 Da or 1,000,000 DA. In some embodiments, the organic molecule may have a mass of less than 500,000 or 300,000 Daltons.

To perform the desorbing step, one will generally expose the matrix:molecule mixture to a source of energy to desorb the large organic molecule from the matrix. The source of energy used for desorption of the large organic molecule will preferably be a laser beam. The laser beam used to desorb and ionize the large organic molecule may be any laser but is preferably a pulsed laser. Typically, the desorption step will include applying an energy of about 20 kV followed by a pulse of energy of about 2.7 kV. Preferably, the pulse of energy comprises light having a wavelength of about 355 nm. The mass of the large organic molecule may then be determined by summing the mass spectra over a number of laser pulses, preferably about 200 laser pulses or about 1000 laser pulses, or any number of pulses therebetween, such as, for example, about 250 laser pulses, about 300 laser pulses, about 350 laser pulses, about 500 laser pulses, about 750 laser pulses, etc. Of course, it is contemplated that one may sum the mass spectra of less than about 200 pulses or more than about 1000 pulses, but it will be understood that lower numbers of pulses, especially very low numbers of pulses such as 10 or 20 or 50 pulses, etc., may give less accurate results, and higher numbers of pulses becomes unnecessarily repetitive and lower the efficiency and cost-effectiveness of the method.

In another aspect, the invention also provides a method for preparing a sample of large organic molecules for mass spectral analysis. This method typically includes providing a solution comprising a large organic molecule to be analyzed, a matrix molecule comprising a volatile, light-absorbing hydroxy-bearing matrix molecule, and a solvent, and evaporating the solvent to provide a solid crystalline matrix containing the molecule to be analyzed.

The present invention applies to MALDI mass spectrometry of all classes of nonvolatile, large organic compounds, with synthetic polymers and biopolymers preferred. The present invention is particularly preferred for mass analysis of biopolymers such as nucleic acids, proteins, PNAs and oligosaccharides due to the fragile nature of these molecules. The method utilizes pulsed laser desorption/ionization mediated by a matrix followed by mass spectrometric separation and detection of the analyte molecules. The matrix may be a crystalline solid or a liquid at room temperature, with crystalline solids being preferred. The preferred matrix has a high sublimation rate in vacuum at room temperature and absorbs the desorption light strongly.

Therefore in accordance with the present invention, there is provided crystalline solid, light absorbing compounds having hydroxy functionalities, but not carboxylic functionalities, for use as a matrix in mass analysis. In preferred embodiments the matrix compounds may be phenols, hydroxyquinolines or hydroxynaphthalenes. The crystalline solids, 8-hydroxyquinoline and 4-nitrophenol, which are volatile at room temperature, are particularly preferred as matrices in accordance with the present invention.

The less energetic, more facile desorption/ionization from these volatile matrices minimizes fragmentation and extends the high mass limit for generation of intact analyte molecules. These crystalline matrices exhibit increased sensitivity for detection of both low (8-hydroxyquinoline) and high (4-nitrophenol) molecular weight analytes. Analyte molecules, including DNA, exceeding 250 kDa molecular weight can be detected by this method.

There is provided embodiments where the analyte is a large organic molecule of greater than about 1,000 Da. Also provided are embodiments where the large organic analyte is a polymer. In certain embodiments the polymer is a biopolymer. In further embodiments the biopolymer is a polynucleic acid, and in still further embodiments the biopolymer is an oligonucleotide. Additionally provided are embodiments where the biopolymer is a protein, polypeptide, or oligosaccharide.

In yet other embodiments, the sample is placed on a cooled sample stage in order to maintain a low vapor pressure of the sample in the vacuum chamber of the mass spectrometer. The sample stage is cooled below about 273° K, more typically between about 170 to about 190° K, and most typically to about 180° K.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
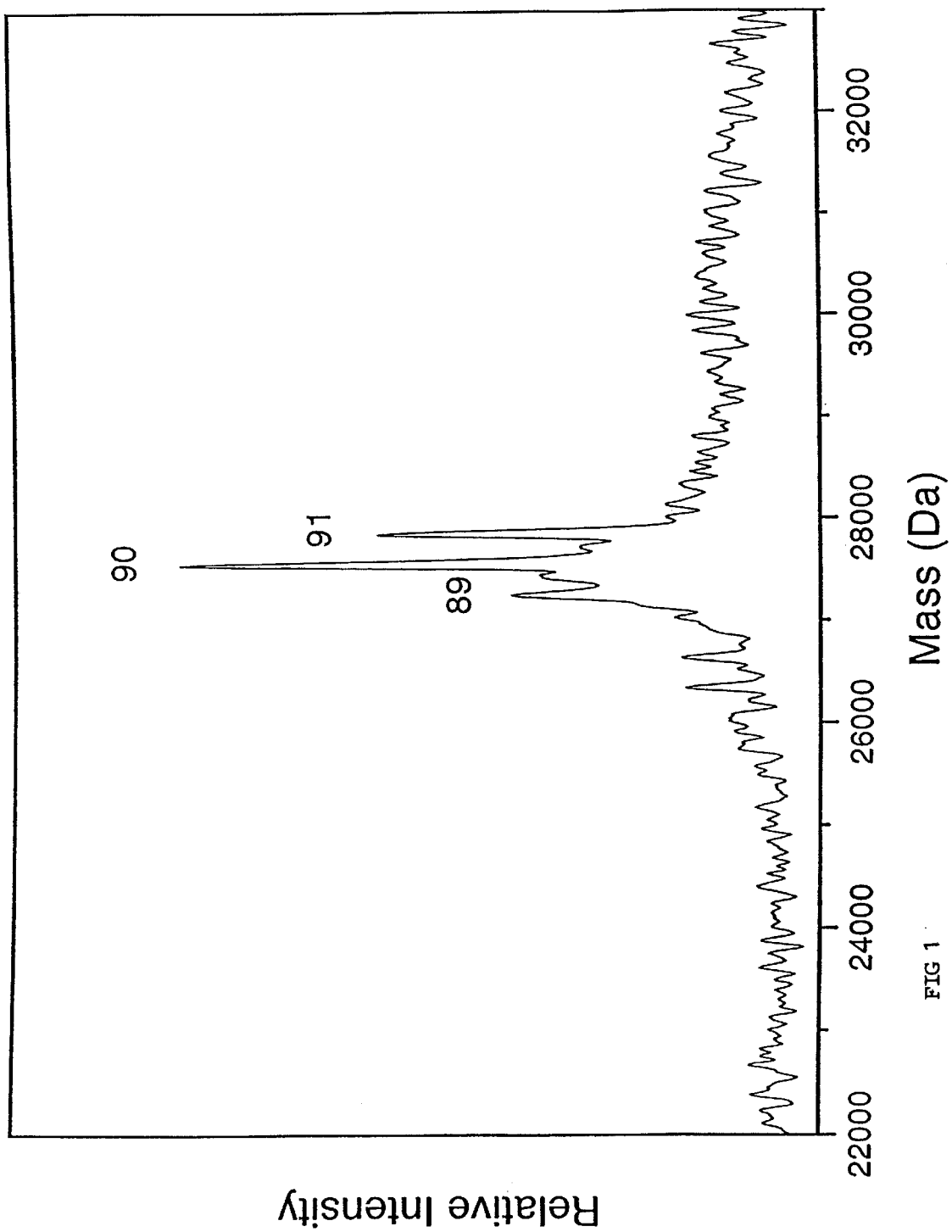
FIG. 1 is a laser desorption/ionization time-of-flight mass spectrum of a mixture of single-stranded DNA oligomers 89, 90, and 91 nucleotides in length obtained using 8-hydroxyquinoline as the matrix. The laser wavelength was 355 nm.

In accordance with the present invention, methods are provided for the preparation of samples for analysis by mass spectroscopy to minimize undesired fragmentation. Select light absorbing molecules, containing hydroxy functionalities (but not carboxylic functionalities) and having significant sublimation rates at room temperature under vacuum, are used as matrices in MALDI mass spectrometry. Hydroxy functionalities offer advantage over carboxylic functionalities due to their increased acidity in the excited state (Huppert et al., 1981) and also typically provide lower intermolecular binding energies to increase volatility. Representative examples of matrix compounds include, but are not limited to, hydroxyquinolines, phenols, and hydroxynaphthalenes.

Samples are prepared by dissolving the analyte in a solution containing the matrix molecule, with the bulk of the solution being one or more solvents which are subsequently allowed to evaporate before mass analysis begins. Typically, the analyte will be present in the solution at a concentration of about 0.05 M to about 1.0 M.

The solvent evaporation may be conducted at a temperature range of about 20° C. to about 30° C., with room temperature, about 25° C. being most preferred. The evaporation results in the formation of a crystalline matrix, composed in part (between about 30% by weight to about 100% by weight) of the subject matrix molecule. Typically the matrix molecular weight is greater than about 90 Da, preferably between about 90 Da and about 400 Da. Due to the high volatility of these matrix molecules under vacuum at room temperature, the samples must be cooled in the mass spectrometers vacuum system to a vapor pressure between about $10^{-10}$ Torr and about $10^{-5}$ Torr, but not exceeding about $10^{-5}$ Torr. These matrix molecules are termed herein as volatile, light-absorbing, hydroxy-bearing matrix molecules. As used herein the term volatile refers to a molecule having a sublimation rate at room temperature of greater than or equal to 0.1 $\mu$m·min$^{-1}$ at a pressure of about $10^{-5}$ Torr or less, and the term light absorbing refers to a molecule having an absorption coefficient greater than about 10 l·cm$^-$ $_1$·mol$^{-1}$.

Two low-sublimation-temperature molecules in particular function effectively as matrices for MALDI of nonvolatile organic molecules for detection by mass spectrometry. The compounds, 8-hydroxyquinoline (8HQ) and 4-nitrophenol (4NP), both contain a hydroxy functional group. The former is especially effective for high-resolution analysis of DNA less than approximately 100 nucleotides (30 kDa), and the latter is especially effective for sensitive detection of higher mass molecules.

Compounds contemplated for analysis using the present invention include a vast array of large organic molecules. As used herein, the term "large organic molecule" refers to a compound having a molecular weight of greater than about 1000 Da. Also as used herein, the term "nonvolatile" refers to a molecule which, when present in its pure, neat form and heated, does not sublimate intact to any significant extent. Also included in the definition of nonvolatile compounds are compounds which, when present in their pure neat form, cannot be practically analyzed by mass spectrometry when conventional gas chromatography methods are employed in the sampling process. Representative of such organic compounds are polynucleic acids, polypeptides, oligosaccharides, PNAs and synthetic polymers. Polymeric compounds are also contemplated for analysis using the present invention. In particular biopolymers which are subject to fragmentation during mass analysis. Representative biopolymers include polymers of amino acids, nucleic acids, saccharides, carbohydrates and polypeptides.

The mass spectrometry may be accomplished by one of several techniques such as time-of-flight, magnetic sector or ion trap. Preferably, the mass spectrometry technique for use with the present invention will be time-of-flight.

The volatility of the matrix crystals necessitates that the sample stage of the mass spectrometer be cooled to substantially below room temperature where the sublimation rate is between about 0.1 $\mu$m·min$^{-1}$ and about 0.1 mm·min$^-$ $_1$. A preferred approach is to use a liquid-nitrogen cooled sample stage, accomplished by flowing liquid nitrogen through a copper sample holder. Thus, the sample is cooled to less than 273° K, preferably between about 170 and 190° K or to about 180° K.

Wavelengths from the ultraviolet to infrared may be employed, depending on the cooled matrix being analyzed. Generally, one of skill in the art will understand that the appropriate wavelength will be one where light absorption is significant for the molecule being analyzed.

The disclosed low-sublimation temperature matrices and methods for using them to determine the mass of a large organic molecule or prepare a large organic molecule for mass spectral analysis may be used in a variety of MS applications, such as MS sequencing of nucleic acids; MS analysis of single nucleotide polymorphisms (SNPs); and MS analysis of simple sequence repeats (SSRs), short tandem repeats (STRs), and microsatellite repeats (MRs).

For example, the methods disclosed herein may be used in nucleic acid sequencing methods involving obtaining nucleic acid fragments using a four base Sanger sequencing reaction, performing MS on the products and determining the nucleic acid sequence from the mass differences between the peaks. The nucleic acid fragments may be obtained by hybridizing a DNA primer to a DNA template and extending the primer by a DNA polymerase in the presence of deoxy- and dideoxy-nucleotides. The DNA template may generally contain the DNA fragment to be sequenced and a region complementary to the primer. The DNA primers may also contain a biotin which allows for capture to a solid phase and a single, chemically cleavable internal linkage (such as a 5'-or 3'-(S)-phosphorothioate linkage which is cleavable by a silver ion catalyzed reaction). The cleavage chemistry of the internal linkage combined with the biotin capture are described in U.S. Pat. No. 5,700,642, incorporate herein by reference.

The nucleic acid fragments may be further processed prior to MS analysis. Generally, these processing steps involve binding the nucleic acid fragments to a streptavidin solid support, washing the bound fragments, and cleaving at the internal cleavage site to release the nucleic acid fragment from the solid support. Typically the bound fragments are first washed with a denaturant, such as aqueous NaOH, to remove unbound DNA and enzyme and then with a series of ammonium acetate washes. Following cleavage, the cleaved extension products may be prepared for MS analysis by drying; mixing the solid residue with the matrix material and ammonium citrate solution; spotting the mixture by pipette onto a plate; and allowing the mixture to dry.

The methods for MS SNP analysis are very similar to the DNA sequencing methods except that only dideoxynucleotides are employed.

These low-sublimation temperature matrices may also be used for analyzing SSRs, STRs, and MRs involving the determination of the number of repetitive units contained in amplification products by MS. The amplification products are typically obtained by hybridizing a DNA primer to a DNA target molecule and extending the primer by a DNA polymerase. Similar to the sequencing methods, the DNA primer contains a region complementary to the DNA target molecule adjacent to the SSR-, STR-, or MR-containing region. The primer may also contain biotin and internal cleavable linkages.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

A time-of-flight mass spectrometer similar to that previously described by Wu et al. (1994) and Hunter et al. (1997) was used, having pulsed delayed ion extraction. The sample stage was floated at 20 kV, and after some delay time (approximately several hundred nanoseconds, dependent on mass), ions were extracted by a 2.7 kV pulse and focused into a 1-meter flight tube. The signal output from the dual microchannel plate detector was amplified and digitized with 5 ns time resolution.

Laser wavelengths of either 355 or 266 nm were employed for desorption/ionization in the examples below. Comparable positive and negative ion signals were observed from oligonucleotide analytes.

The temperature of the sample on a liquid nitrogen-cooled sample stage was maintained at approximately 180 K as measured by thermocouple wires, low enough to maintain a matrix vapor pressure of less than $10^{-5}$ Torr.

Example 2

DNA Oligomer Analysis Employing 8-Hydroxyquinoline as a Matrix

The preparative solution for the 8HQ matrix began by using 0.2 M 8HQ in 1:1 (volume) acetone:butanone. To reduce alkali-metal adduct ion formation, to that initial 8HQ solution was added an equal volume of 50 mM aqueous diammonium citrate, resulting in a 25 mM final diammonium citrate concentration and 0.1 M 8HQ concentration. 8HQ is known to chelate trace amounts of metal ions, especially copper, but the addition of CDTA (trans-1,2-diaminocyclohexane-N,N,N',N' tetraacetic acid monohydrate) effectively suppressed copper adducts in the mass spectrum; a small aliquot of concentrated CDTA was added to a much larger volume of the 8HQ solution to yield a 10 mM CDTA concentration.

The oligonucleotide sample was obtained from polymerase chain reaction (PCR) amplification of a short tandem repeat sequence at the human TH01 (tyrosine hydroxylase gene) locus. One of the strands was captured, denatured, washed, then released to produce single-stranded products. An aliquot of aqueous solution of this TH01 oligonucleotide (estimated 10 pmol quantity) was first evaporated in a vacuum evaporator to remove the water, and then one microliter of the matrix solution was added to the dried DNA. This resulting solution was pipetted onto a silicon substrate mounted on a copper sample holder. After air-drying of the solvent and resultant crystallization of the matrix, the sample was placed on the cryogenically-cooled sample stage in the mass spectrometer.

8HQ is an effective matrix for high resolution studies of DNA oligomers less than approximately 100 nucleotides in length. FIG. 1 illustrates the mass resolution attainable for single-stranded oligonucleotides of about 27 kDa using 355 nm pulsed laser light for desorption and summing mass spectra over 200 laser pulses. DNA oligomers containing 89, 90, and 91 nucleotides have a mass resolution (m/Δm) of 650, 625, and 700, respectively at full width at half height. Spectra of oligonucleotides in 8HQ matrix typically have a low background ion signal and high signal-to-noise levels.

Example 3

DNA Oligomer Analysis Employing 4-Nitrophenol as a Matrix

Figure 2:
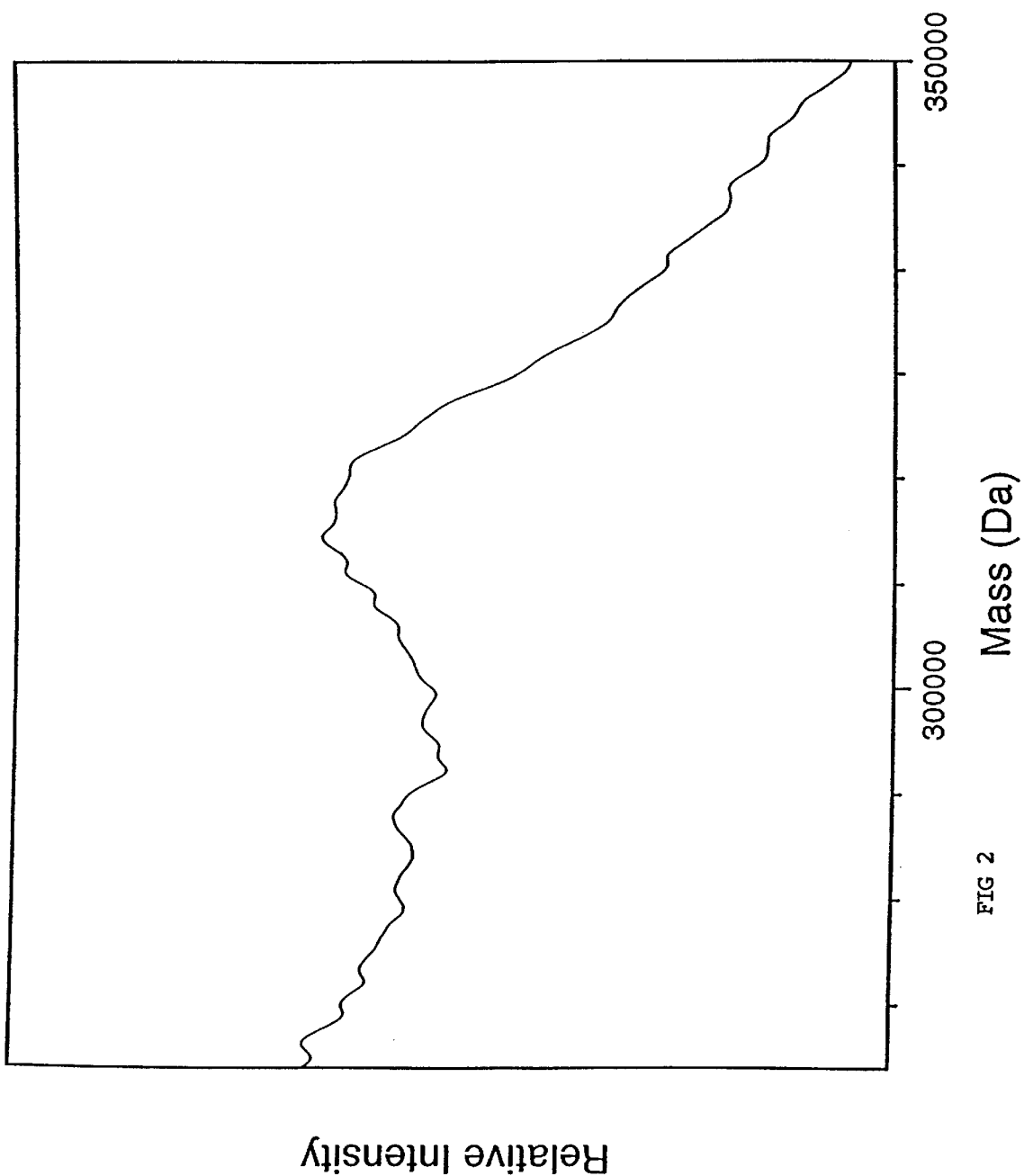
FIG. 2 is a laser desorption/ionization time-of-flight mass spectrum of a double-stranded PCR product at 315 kDa per strand (greater than approximately 1000 nucleotides in length) using a 4-nitrophenol matrix. The laser wavelength was 355 nm.

The preparative solution for the 4NP matrix was 0.5 M 4NP in 1:1 (volume) methanol:water containing diammonium citrate at 50 mM final concentration. One microliter of the matrix solution was added to dried DNA which was a double-stranded PCR product estimated at 10 pmol quantity derived from an unknown cDNA insert in a vector. This resulting solution was pipetted onto a silicon substrate mounted on a copper sample holder. After air-drying of the solvent and resultant crystallization of the matrix, the sample was placed on the cryogenically-cooled sample stage in the mass spectrometer. FIG. 2 is the resulting time-of-flight mass spectrum using 355 nm laser light for desorption and summing over 1000 laser pulses yielding an estimated mass of 315 kDa which corresponds to an estimated number of bases exceeding 1,000. The width of the peak originates in part from the mass difference of the two complementary DNA strands (denatured during analysis) and partly from adduct formation as well as fragmentation. DNA oligomers have not previously been reported to be detected in this size range.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,920,264 to Becker.
U.S. Pat. No. 5,118,937 to Hillenkamp et al.
U.S. Pat. No. 5,135,870 to Williams et al.
Abrams et al., "Comprehensive Detection of Single Base Changes in Human Genomic DNA Using Denaturing Gradient Gel Electrophoresis and a GC Clamp," *Genomics*, 7:463–475, (1990).
Gimon et al., "Are Proton Transfer Reactions of Excited States Involved in UV Laser Desorption Ionization?," *Organic Mass Spectrometry*, 27:827–830 (1992).
Hunter et al., "Cryogenic Frozen Solution Matrices for Analysis of DNA by Time-of-Flight Mass Spectrometry," *Analytical Chemistry*, 69:3608–12 (1997).
Huppert et al., "Laser Studies of Proton Transfer," *Advances in Chemical Physics*, 47:643–679 (1981).
Liu et al. "Use of a Nitrocellulose Film Substrate in Matrix-Assisted Laser Desorption/Ionization Mass Spectrometry for DNA Mapping and Screening," *Analytical Chemistry*, 67:3482–3490 (1995).
Nelson et al., "Detection of Human IgM at m/z~1 MDa," *Rapid Communications in Mass Spectrometry*, 9:625 (1995).
Orita et al., "Detection of Polymorphisms of Human DNA by Gel Electrophoresis as Single-Strand Conformation Polymorphisms," *Proc. Natl. Acad. Sci. USA*, 86:2766–2770, 1989
Saleeba et al., "Chemical Cleavage of Mismatch to Detect Mutations," *Methods Enzymology*, 217:286–295 (1993).
Spengler et aL, "Laser Mass Analysis in Biology," *Ber. Bunsenqes Phys. Chem.*, 93(3):396–402, (1989).
Tanaka et al., "Protein and Polymer Analyses up to m/z 100 000 by Laser Ionization Time-of-flight Mass Spectrometry," *Rapid Commun. in Mass Spectrometry*, 2:151–153 (1988).
Tang et al. "Detection of 500-Nucleotide DNA by Laser Desorption Mass Spectrometry," *Rapid Communications in Mass Spectrometry*, 8:727–730 (1994).
Wu et al. "Matrix-Assisted Laser Desorption Time-of-Flight Mass Spectrometry of Oligonucleotides Using 3-Hydroxypicolinic Acid as an Ultraviolet-Sensitive Matrix," *Rapid Communications in Mass Spectrometry*, 7:142–146 (1993).
Wu et al. "Time-of-Flight Mass Spectrometry of Underivatized Single-Stranded DNA Oligomers by Matrix-Assisted Laser Desorption," *Analytical Chemistry*, 66:1637–1645 (1994).
Youil et al., "Screening for Mutations by Enzyme Mismatch Cleavage with T4 Endonuclease VII," *Proc. Natl. Acad. Sci. USA*, 92:87–91 (1995).

What is claimed is:

1. Components for the preparation of a large organic molecule for analysis by mass spectrometry, the components comprising:

a volatile matrix comprising a photoabsorbing low-sublimation temperature matrix;

one or more solvents; and a sample stage capable of being cooled.

2. The components of claim 1, wherein the volatile matrix comprises a volatile, light-absorbing, hydroxy-bearing matrix.

3. The components of claim 1, wherein the volatile matrix is selected from the group consisting of phenols, hydroxyquinolines, and hydroxynaphthalenes.

4. The components of claim 3, wherein the volatile matrix comprises 4-nitrophenol.

5. The components of claim 3, wherein the volatile matrix comprises 8-hydroxyquinoline.

6. The components of claim 1, wherein the volatile matrix has a molecular weight of between about 90 Da and about 400 Da.

7. The components of claim 1, wherein a sublimation rate of the volatile matrix is at least 0.1 $\mu$M/min at a pressure of about $10^{-5}$ Torr.

8. The components of claim 1, wherein a sublimation rate of the volatile matrix is between about 0.01 $\mu$M/min to about 0.1 $\mu$M/min.

9. The components of claim 1, wherein the volatile matrix comprises a photoabsorbing matrix capable of absorbing light having a wavelength between about 200 nm and 20,000 nM.

10. The components of claim 1, wherein the volatile matrix comprises a photoabsorbing matrix having an absorption coefficient between about 10 L/cm/mol and about $10^6$ L/cm/mol.

11. The components of claim 1, wherein the one or more solvents comprise one or more of water, methanol, ethanol, toluene, acetone, or acetonitrile.

12. The components of claim 1, wherein the one or more solvents comprises diammonium citrate, trans-1,2-diaminocyclohexane-N,N,N',N' tetraacetic acid monohydrate, or a combination thereof.

13. The components of claim 1, wherein the solvent comprises 1:1 acetone:butanone.

14. The components of claim 1, wherein the sample stage comprises a liquid nitrogen-cooled sample stage.

15. The components of claim 1, wherein the sample stage comprises a copper sample holder.

16. The components of claim 1, wherein the sample stage comprises a silicon substrate.

17. The components of claim 1, wherein the large organic molecule comprises one or more biomolecules or synthetic polymers.

18. The components of claim 17, wherein the one or more biomolecules comprise a nucleic acid, a polypeptide, a peptide nucleic acid, an oligosaccharide, or a mass-modified derivative thereof.

19. The components of claim 18, wherein the nucleic acid comprises DNA or RNA.

20. The components of claim 1, further comprising:

a solid support capable of binding the large organic molecule; and a washing solvent.

21. The components of claim 20, wherein the large organic molecule comprises biotin and the solid support comprises a biotin-binding moiety.

22. The components of claim 21, wherein the biotin-binding moiety comprises streptavidin.

23. The components of claim 1, further comprising one or more of a DNA primer, a biotin-linked DNA primer, a DNA polymerase, a denaturant, aqueous NaOH, ammonium acetate, and ammonium citrate.

* * * * *

UNITED STATES PATENT AND TRADEMARK OFFICE
CERTIFICATE OF CORRECTION

PATENT NO.    : 6,265,716 B1
DATED         : July 24, 2001
INVENTOR(S)   : Hunter, J.M., Lin and H., Becker, C.H.

It is certified that error appears in the above-identified patent and that said Letters Patent is hereby corrected as shown below:

<u>Column 14,</u>
Lines 36-39, Claim 9, should read as follows:

9. The components of claim 1, wherein the volatile matrix comprises a photoabsorbing matrix capable of absorbing light having a wavelength between about 200 nm and 20,000 nm.

Signed and Sealed this

Ninth Day of September, 2003

JAMES E. ROGAN
*Director of the United States Patent and Trademark Office*